United States Patent [19]

Klotz

[11] 4,377,502

[45] Mar. 22, 1983

[54] SYNTHESIS OF CRYSTALLINE ALUMINOSILICATE MOLECULAR SIEVES

[75] Inventor: Marvin R. Klotz, Batavia, Ill.

[73] Assignee: Standard Oil Company (Indiana), Chicago, Ill.

[21] Appl. No.: 218,276

[22] Filed: Dec. 19, 1980

Related U.S. Application Data

[63] Continuation-in-part of Ser. No. 107,145, Dec. 26, 1979, abandoned, and a continuation-in-part of Ser. No. 107,147, Dec. 26, 1979, abandoned.

[51] Int. Cl.³ .................... C01B 33/28; B01J 29/06
[52] U.S. Cl. ........................ 252/455 Z; 423/328; 423/329
[58] Field of Search .................. 423/328–330; 252/431 N, 455 Z; 260/448 C

[56] References Cited

U.S. PATENT DOCUMENTS

| | | | |
|---|---|---|---|
| 3,130,007 | 4/1964 | Breck | 423/329 |
| 3,271,418 | 9/1966 | Plank et al. | 208/120 |
| 3,578,723 | 5/1971 | Bowes et al. | 423/328 |
| 3,702,886 | 11/1972 | Argauer et al. | 423/328 |
| 4,000,248 | 12/1976 | Martin | 423/329 |
| 4,046,859 | 9/1977 | Plank et al. | 423/328 |
| 4,199,556 | 4/1980 | Plank et al. | 423/329 |
| 4,242,233 | 12/1980 | Ball et al. | 423/329 X |

FOREIGN PATENT DOCUMENTS 1365318  8/1974  United Kingdom ............... 423/329

OTHER PUBLICATIONS

Kibby et al, "Journal of Catalysis", 35, 256–272, 1974.
Wolf et al, "Zeitschrift fur Chemie", 13 Jg (1973), pp. 109 & 110.
Charnell, "J. Crystal Growth", 8 (1971), pp. 291–293.

Primary Examiner—Edward J. Meros
Attorney, Agent, or Firm—Wallace L. Oliver; William T. McClain; William H. Magidson

[57] ABSTRACT

Crystalline aluminosilicate molecular sieves are prepared by (1) forming an aqueous mixture of an oxide of aluminum, an oxide of silicon, a metal or ammonium cation and a suitable oxygen-containing monomeric organic template compound, (2) maintaining the pH of such mixture between 9 and 14, and (3) crystallizing the mixture. The organic templates include ethanolamine, diethanolamine, triethanolamine, ethylethanolamine, ethyldiethanolamine, 2-amino-2-ethyl-1,3-propanediol, morpholine, and alkali metal complexed tetrahydrofuran, dioxane, dioxolane, and crown ethers. Crystalline aluminosilicates prepared include mordenite, ferrierite, ZSM-4, and ZSM-5.

28 Claims, No Drawings

SYNTHESIS OF CRYSTALLINE ALUMINOSILICATE MOLECULAR SIEVES

CROSS REFERENCE TO RELATED APPLICATIONS

This is a continuation-in-part to U.S. Application Ser. Nos. 107,145 and 107,147 both filed Dec. 26, 1979 and now abandoned, which are incorporated by reference herein.

BACKGROUND OF THE INVENTION

This invention relates to a new method of preparing crystalline aluminosilicate molecular sieve compositions.

Zeolitic materials, both natural and synthetic, are known to have catalytic capabilities for many hydrocarbon processes. Zeolitic materials typically are ordered porous crystalline aluminosilicates having a definite structure with large and small cavities interconnected by channels. The cavities and channels throughout the crystalline material generally are uniform in size allowing selective separation of hydrocarbons. Consequently, these materials in many instances are known in the art as "molecular sieves" and are used, in addition to selective adsorptive processes, for certain catalytic properties. The catalytic properties of these materials are affected to some extent by the size of the molecules which selectively penetrate the crystal structure, presumably to contact active catalytic sites within the ordered structure of these materials.

Generally, the term "molecular sieve" includes a wide variety of both natural and synthetic positive-ion-containing crystalline zeolite materials. They generally are characterized as crystalline aluminosilicates which comprise networks of tetrahedra of $SiO_4$ and $AlO_4$ moieties in which silicon and aluminum atoms are cross-linked by sharing of oxygen atoms. The electrovalence of the aluminum atom is balanced by the use of positive ions, for example, alkali-metal or alkaline-earth-metal cations, ammonium ions, or hydrogen ions.

Prior art developments have resulted in the formations of many synthetic zeolitic crystalline materials. Crystalline aluminosilicates are the most prevalent and, as described in the patent literature and in the published journals, are designated by letters or other convenient symbols. Examples of these materials are Zeolite A (U.S. Pat. No. 2,882,243), Zeolite X (U.S. Pat. No. 2,882,244), Zeolite Y (U.S. Pat. No. 3,130,007), Zeolite ZSM-4 (U.S. Pat. No. 3,578,723), Zeolite ZSM-5 (U.S. Pat. No. 3,702,886), Zeolite ZSM-11 (U.S. Pat. No. 3,709,979), Zeolite ZSM-12 (U.S. Pat. No. 3,832,449), and others.

The present invention is a new method of preparing crystalline aluminosilicate molecular sieve compositions using oxygen-containing organic compounds as templates in which the silica/alumina ($SiO_2/Al_2O_3$) ratio can be adjusted to effect better selectivity in hydrocarbon conversion reactions. The crystalline forms, as determined from X-ray diffraction analysis, of these compositions include mordenite-like and ferrierite-like forms and forms exhibited in aluminosilicates identified as ZSM-4 and ZSM-5.

Molecular sieves characterized as "mordenite" by chemical composition and X-ray spectra are known as naturally occurring materials and as synthesized materials. For example, a conventional mordenite sieve is produced by crystallizing a basic mixture of sodium aluminate and an oxide of silicon without the use of an organic template compound. Such mordenites are described in D. W. Breck "Zeolite Molecular Sieves," John Wiley & Sons, 1974, incorporated by reference herein. U.S. Pat. No. 4,061,717 discloses a method of producing a mordenite molecular sieve using an ionene polymer as an organic template compound in the crystallization of the sieve. U.S. Pat. No. 4,107,195 discloses synthetic mordenite prepared as a by-product using 1,4-butanediamine, ethylenediamine and pyrrolidine as organic templates.

Molecular sieves characterized as "ferrierite" by chemical composition and X-ray spectra are known as naturally occurring materials and as synthesized materials. For example, a conventional ferrierite sieve is produced by crystallizing a basic mixture of sodium aluminate and an oxide of silicon without the use of an organic template compound. Such mordenites are described in D. W. Breck "Zeolite Molecular Sieves," John Wiley & Sons, 1974, incorporated by reference herein. U.S. Pat. No. 4,000,248 discloses a method of producing a ferrierite molecular sieve using N-methyl pyridinium hydroxide as an organic template compound in the crystallization of the sieve. U.S. Pat. Nos. 4,016,245, 4,107,195 and 4,046,859 disclose the formation of a ferrierite-like material using an organic template derived from ethylenediamine, pyrrolidine or butanediamine, or organometallic 2-(hydroxyalkyl)-trialkylaluminum compounds.

Aluminosilicate molecular sieves identified as ZSM-5 are described in U.S. Pat. Nos. 3,702,886 and 4,139,600. Such aluminosilicates are prepared using organic templates such as tetralkyl ammonium salts, primary alkyl amines and alkylene diamines as described in U.S. Pat. Nos. 4,139,600 and 4,151,189. Aluminosilicate molecular sieve identified as ZSM-4 is described in U.S. Pat. Nos. 3,578,723 and 4,021,447 using organic templates including tetraalkyl ammonium salts, pyrrolidine and choline salts.

SUMMARY OF THE INVENTION

What has been discovered is a method to prepare crystalline aluminosilicate molecular sieves comprising (1) forming an aqueous mixture of an oxide of aluminum, an oxide of silicon, a metal or ammonium cation and a suitable oxygen-containing monomeric organic template compound, (2) maintaining the pH of such mixture between 9 and 14, and (3) crystallizing the mixture.

BRIEF DESCRIPTION OF THE INVENTION

The present invention is a method of producing a molecular sieve using simple oxygen-containing organic compounds as templates.

Further, this invention is a method of producing a series of crystalline aluminosilicate molecular sieve compositions using identical organic template compounds during crystallization, but yielding crystalline compositions with different X-ray diffraction patterns. By using the oxygen-containing organic template compounds disclosed in this invention and controlling variables such as the silica/alumina ratios in the crystallization mixture, a series of crystalline aluminosilicate molecular sieves can be produced including aluminosilicates identified as ZSM-4, ZSM-5, mordenite and ferrierite. This invention shows that these aluminosilicates are interrelated in that all can be produced under similar conditions using the same organic template compound but changing the silica/alumina ratio in the crystallization mixture. It is observed that as the silica/alumina ratio increases the aluminosilicate usually formed during crystallization of this invention changes in the order: ZSM-5, ferrierite, mordenite, ZSM-4.

A sieve prepared according to this invention is characterized as a crystalline aluminosilicate having the following chemical composition in terms of oxides:

$$0.9 \pm 0.2 M_{2/n}O : Al_2O_3 : ySiO_2 : zH_2O$$

wherein M is at least one cation of valence n, y is between about 2 and about 500, and z is between 0 and about 160, preferably between 0 and 40.

Significant lines of the X-ray diffraction pattern of a typical mordenite (obtained from material prepared in Example I) are given in Table I, while significant X-ray diffraction lines of a typical ferrierite (obtained from material prepared in Example VII) are given in Table II. Table III shows significant lines of a typical X-ray diffraction pattern of an aluminosilicate identified as ZSM-4 prepared according to this invention, while Table IV shows typical significant X-ray diffraction lines of an aluminosilicate identified as ZSM-5 prepared according to this invention.

The X-ray powder diffraction measurements shown in Tables I–IV were obtained on a Phillips diffractometer using copper K alpha radiation in conjunction with an AMR focusing monochromometer and a theta angle compensating slit in which aperture varies with theta angle. Data generated by the diffractometer were processed through a Canberra hardware/software package and presented in a strip chart and in a numerical printout of relative intensity (peak height), interplanar spacing and two-theta angle. The compensating slit and the Canberra package tend to increase the peak-to-background ratios while reducing the peak intensities at low theta angles [large interplanar spacings] and increasing the peak intensities at high theta angles [small interplanar spacings].

In reporting the results obtained, relative intensities (i.e., relative peak heights), were arbitrarily assigned the following values:

| Relative Peak Height | Assigned Strength |
|---|---|
| less than 10 | VW (very weak) |
| 10–19 | W (weak) |
| 20–39 | M (medium) |
| 40–69 | MS (medium strong) |
| 70–89 | S (strong) |
| greater than 90 | VS (very strong) |

Interplanar spacings are represented by "d" and are expressed in terms of Angstrom units (Å) and nanometers (nm).

TABLE I

| d-spacing | | | |
|---|---|---|---|
| Å | nm | I/Io | Assigned Strength |
| 9.28 | 0.928 | 33 | M |
| 6.66 | 0.666 | 34 | M |
| 4.57 | 0.457 | 33 | M |
| 4.02 | 0.402 | 67 | MS-S |
| 3.49 | 0.349 | 100 | VS |
| 3.41 | 0.341 | 65 | MS-S |
| 3.24 | 0.324 | 74 | MS-S |
| 2.91 | 0.291 | 34 | M |
| 2.52 | 0.252 | 24 | M |

TABLE I-continued

| d-spacing | | | |
|---|---|---|---|
| Å | nm | I/Io | Assigned Strength |
| 2.05 | 0.205 | 22 | M |
| 1.88 | 0.188 | 22 | M |

TABLE II

| d-spacing | | | |
|---|---|---|---|
| Å | nm | I/Io | Assigned Strength |
| 9.54 | 0.954 | 91 | S-VS |
| 7.04 | 0.704 | 47 | MS |
| 6.65 | 0.665 | 30 | M |
| 5.72 | 0.572 | 20 | M |
| 3.98 | 0.398 | 71 | MS-S |
| 3.78 | 0.378 | 56 | MS |
| 3.65 | 0.365 | 29 | M |
| 3.54 | 0.354 | 100 | VS |
| 3.48 | 0.348 | 76 | S |
| 3.32 | 0.332 | 27 | M |
| 3.13 | 0.313 | 40 | M-MS |
| 3.04 | 0.304 | 25 | M |
| 1.99 | 0.199 | 24 | M |
| 1.92 | 0.192 | 24 | M |

TABLE III

| d-spacing | | |
|---|---|---|
| Å | nm | Assigned Strength |
| 9.2 | 0.92 | MS |
| 7.96 | 0.796 | W |
| 6.85 | 0.685 | MS |
| 5.99 | 0.599 | M |
| 5.57 | 0.557 | M |
| 5.00 | 0.500 | W |
| 4.71 | 0.471 | M |
| 4.37 | 0.437 | M |
| 4.18 | 0.418 | W |
| 3.80 | 0.380 | M |
| 3.70 | 0.370 | MS |
| 3.51 | 0.351 | VS |
| 3.43 | 0.343 | MS |
| 3.16 | 0.316 | S |
| 3.08 | 0.308 | MS |
| 2.92 | 0.292 | VS |

TABLE IV

| d-spacing | | |
|---|---|---|
| Å | nm | Assigned Strength |
| 11.4 | 1.14 | MS |
| 10.2 | 1.02 | M |
| 7.5 | 0.75 | VW |
| 7.1 | 0.71 | VW |
| 6.4 | 0.64 | W |
| 6.06 | 0.606 | W |
| 5.74 | 0.574 | W |
| 5.64 | 0.564 | W |
| 5.01 | 0.501 | VW |
| 4.62 | 0.462 | VW |
| 4.39 | 0.439 | W |
| 3.87 | 0.387 | VS |
| 3.76 | 0.376 | MS |
| 3.07 | 0.307 | W |
| 3.00 | 0.300 | M |

The crystalline aluminosilicate molecular sieves prepared according to this invention is formed by crystallizing an aqueous mixture, at a controlled pH, of a source of cations, an oxide of aluminum, an oxide of silicon, and an organic template compound.

The method of this invention for preparing crystalline aluminosilicate molecular sieves can form such sieves in different crystalline form depending on starting materials and reaction conditions. Typically, for a specific template compound, ferrierite-like material is formed preferentially using silica/alumina ratios higher than that employed for mordenite production. Thus, for a monobasic template compound, mordenite usually is formed at a $SiO_2/Al_2O_3$ of about 16 while ferrierite usually is formed at a $SiO_2/Al_2O_3$ of about 32. However, using a dibasic template will shift the typical $SiO_2/Al_2O_3$ ratio for mordenite to about 8 and for ferrierite to about 16.

Other factors which may affect production of a crystalline form include the cation and water concentrations in the crystallization mixture, and the crystallization time and temperature.

By further alteration of the $SiO_2/Al_2O_3$ ratio in a crystallization mixture, still different crystalline forms can be made. For example, using a monobasic template at lower $SiO_2/Al_2O_3$ ratios, an aluminosilicate identified as ZSM-4 can be made having X-ray diffraction lines listed in Table III and a $SiO_2/Al_2O_3$ ratio of about 3 to 60 and typically about 8. At higher $SiO_2/Al_2O_3$ ratios using a monobasic template, an aluminosilicate identified as ZSM-5 can be made having X-ray diffraction lines listed in Table IV and $SiO_2/Al_2O_3$ ratios of about 5–500 and typically between about 35 and 100. If a dibasic template is used in the method of this invention, the typical $SiO_2/Al_2O_3$ range for a specific crystalline form shifts downward by a factor of two.

Generally, in the crystallization mixture of the preparations conducted according to this invention the $OH^-/SiO_2$ ratio is between about 0.005 and 10 while the $H_2O/OH^-$ ratio is between about 10 and 4000; the $SiO_2/Al_2O_3$ ratio can be about 2 to 1000. Further, the $R_2O^+/[R_2O^+ + M_{2/n}O]$ ratio is between about 0.1 and 1.0 where R is an organic compound and M is at least one cation having a valence n. Generally, about half of the aluminum present in a crystallization mixture is incorporated into a crystalline aluminosilicate product.

Typically, the mole ratios of the various reactants can be varied to produce the mordenite crystalline aluminosilicate of this invention. Specifically, the mole ratios of the initial reactant concentrations are indicated below:

|  | Broad | Preferred | Most Preferred |
|---|---|---|---|
| $SiO_2/Al_2O_3$ | 2–128 | 8–40 | 16–32 |
| $R_2O^+/[R_2O^+ + M_{2/n}O]$ | 0.1–1.0 | 0.2–0.95 | 0.2–0.95 |
| $OH^-/SiO_2$ | 0.005–10 | 0.01–3 | 0.01–3 |
| $H_2O/OH^-$ | 10–4000 | 10–500 | 10–500 | where R is an organic compound and M is at least one cation having a valence n, such as an alkali metal or an alkaline earth metal cation.

By regulation of the quantity of aluminum (represented as $Al_2O_3$) in the reaction mixture, it is possible to vary the $SiO_2/Al_2O_3$ molar ratio in the final product in a range of from about 2 to about 65 and preferably from about 4 to about 20 and most preferably about 8 to about 16.

Typically, the mole ratios of the various reactants can be varied to produce the ferrierite crystalline aluminosilicates of this invention. Specifically, the mole ratios of the initial reactant concentrations are indicated below:

|  | Broad | Preferred | Most Preferred |
|---|---|---|---|
| $SiO_2/Al_2O_3$ | 2–256 | 15–80 | 32–64 |
| $R_2O^+/[R_2O^+ + M_{2/n}O]$ | 0.1–1.0 | 0.2–0.95 | 0.2–0.95 |
| $OH^-/SiO_2$ | 0.005–10 | 0.01–3 | 0.01–3 |
| $H_2O/OH^-$ | 10–4000 | 10–500 | 10–500 | where R is an organic compound and M is at least one cation having a valence n, such as an alkali metal or an alkaline earth metal cation.

By regulation of the quantity of aluminum (represented as $Al_2O_3$) in the reaction mixture, it is possible to vary the $SiO_2/Al_2O_3$ molar ratio in the final product in a range of from about 2 to about 125 and preferably from about 8 to about 40 and most preferably about 16 to about 32.

More specifically, the material of the present invention is prepared by mixing a cation source compound, an aluminum oxide source, and an organic template compound in water (preferably distilled or deionized). The order of addition usually is not critical although a typical procedure is to dissolve sodium hydroxide and sodium aluminate in water and then add the template compound. Generally, after adjusting the pH, the silicon oxide compound is added with intensive mixing such as that performed in a Waring Blender. After the pH again is checked and adjusted, the resulting slurry is transferred to a stirred, closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 14. Advantageously, the pH of the reaction system falls within the range of about 10.5 to about 13.0.

Examples of oxides of silicon useful in this invention include silicic acid, sodium silicate, tetraalkyl silicates and Ludox, a stabilized polymer of silicic acid manufactured by E. I. duPont de Nemours & Co. Typically, the oxide of aluminum source is sodium aluminate although equivalent species can be used such as a mixture of sodium hydroxide and aluminum sulfate.

Useful cations in this invention include alkali metal and alkaline earth metal cations such as sodium, potassium, calcium and magnesium. Ammonium cations may be used in conjunction with such metal cations. Since basic conditions are required for crystallization of the molecular sieve of this invention, the source of such cation usually is a hydroxide such as sodium hydroxide.

Organic template compounds useful in this invention are cyclic or acyclic, alkyl or aryl, oxygen-containing organic compounds which may be coupled with a Group IA metal cation including oxygen-containing organic amines and ether complexed alkali metal cations such as sodium, potassium or lithium.

More specifically, useful organic templates include:
(a) hydroxy amines of the structure

wherein R is an alkyl group containing from two to about six carbon atoms and at least one hydroxyl group; and R' and R" are hydrogen or an alkyl group containing two to about six carbon atoms and zero to about two oxygen atoms;

(b) hydroxy diamines of the structure

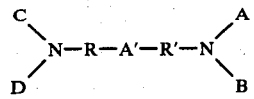

wherein A' is an aryl group or an alkylene group containing two to about twelve carbon atoms; R and R' are alkylene groups containing from zero to about six carbon atoms; and A, B, C, and D are hydrogen or alkyl groups containing one to four carbon atoms and up to about two hydroxyl groups provided at least one such alkyl group contains a hydroxyl group;

(c) saturated cyclic amines containing up to about ten carbon atoms and containing one or two oxygen atoms; and (d) ethers, preferably cyclic ethers, containing up to about twelve carbon atoms, complexed with a Group IA metal cation.

In cation-complexed ethers, the source of metal cation typically is the metal cation existing in the crystallization solution. Thus, the cation source usually is the sodium hydroxide or sodium aluminate used in forming the sieve.

Examples of useful organic templates include ethanolamine, diethanolamine, triethanolamine, ethylethanolamine, ethyldiethanolamine, 2-amino-2-ethyl-1,3-propanediol, morpholine, and alkali metal ion complexed tetrahydrofuran, dioxane, dioxolane and crown ethers.

Generally, corresponding germanium compounds can be substituted for the silicon oxides and corresponding gallium compounds can be substituted for the aluminates as described herein.

In a more detailed description of a typical preparation of this invention, suitable quantities of sodium hydroxide and sodium aluminate are dissolved in distilled or deionized water followed by addition of the organic template. Preferably, the pH is adjusted between 10.5 and 13 using a compatible base or acid such as sodium bisulfate or sodium hydroxide. After sufficient quantities of silicate acid polymer (Ludox) are added with intensive mixing, preferably the pH is again checked and adjusted to a range of about 10.5 to 13.0, preferably about 10.5 to 11.5. The resulting slurry is transferred to a closed crystallization vessel and moderately stirred at a pressure at least the vapor pressure of water for a time sufficient to permit crystallization which usually is about 0.25 to about 20 days, typically is about one to about ten days and preferably is about five to about seven days, at a temperature ranging from about 100° to about 250° C., preferably about 125° to about 200° C. Preferably, the crystallization temperature is maintained below the decomposition temperature of the organic template compound. Especially preferred conditions are stirring at about 165° C. for about five to about seven days. Samples of material can be removed during crystallization to check the degree of crystallization and determine the optimum crystallization time.

The crystalline material formed can be separated and recovered by well-known means such as filtration with washing. This material can be mildly dried for anywhere from a few hours to a few days at varying temperatures, typically about 50°–200° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, the mildly dried product is calcined at temperatures ranging from about 260° C. to about 850° C. and preferably about 525° to about 600° C. Extreme calcination temperatures or prolonged crystallization times may prove detrimental to the crystal structure or may totally destroy it. Generally there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about four hours.

The crystalline aluminosilicates prepared according to this invention can be used as catalysts or as adsorbents whether in the alkali-metal or alkaline-earth-metal forms, the ammonium form, the hydrogen form, or any other univalent or multivalent cationic form. Mixtures of cations may be employed.

A catalytically active material can be placed onto the aluminosilicate structure by ion exchange, impregnation, a combination thereof, or other suitable contact means. Advantageously, before placing a catalytically active metal ion or compound on the aluminosilicate structure, the aluminosilicate is in the hydrogen form which, typically, is produced by exchange with ammonium ion followed by calcination.

The original cation in the crystalline aluminosilicate prepared according to this invention, which usually is sodium ion, can be replaced by ion exchange with other cations including other metal ions and their amine complexes, alkylammonium ions, ammonium ions, hydrogen ions, and mixtures thereof. Preferred replacing cations are those which render the crystalline aluminosilicate catalytically active, especially for hydrocarbon conversion. Typical catalytically active ions include hydrogen, metal ions of Groups IB, IIB, IIIA and VIII, and of manganese, vanadium, chromium, uranium, and rare earth elements.

Also water soluble salts of catalytically active materials can be impregnated onto the crystalline aluminosilicate of this invention. Such catalytically active materials include hydrogen, metals of Groups IB, IIB, IIIA, IVB, VB, VIB, VIIB and VIII, and rare earth elements.

Ion exchange and impregnation techniques are well known in the art. Typically, an aqueous solution of a cation species is exchanged one or more times at about 85° to about 100° C. Impregnation of a catalytically active compound on the aluminosilicate or on a composition comprising the crystalline aluminosilicate suspended in and distributed throughout a matrix of a support material such as a porous refractory inorganic oxide such as alumina, often results in a suitable catalytic composition.

The choice of catalytically active materials to be placed on the crystalline aluminosilicate depends on the intended process use. For example, for hydrocarbon conversion processes such as xylene isomerization and isomerization of ethylbenzene to xylenes, metal ions such as Group VIII metal ions can be exchanged onto the crystalline aluminosilicate. Also compounds of catalytically active metal compounds such as oxides of molybdenum, chromium and tungsten can be impregnated on the crystalline aluminosilicate prepared according to this invention. A combination of ion exchange and impregnation can be used.

The amount of catalytically active metal placed on the aluminosilicate of this invention can vary from less than one weight percent to about thirty weight percent, typically from about 0.05 to about 25 weight percent, depending on the process use intended. The optimum amount can be determined easily by routine experimentation.

If desired, a hydrogenating component, such as ions or compounds of tungsten, vanadium, molybdenum, rhenium, nickel, cobalt, chromium, manganese, a noble metal such as platinum or palladium, or a rare earth element, can be ion exchanged, impregnated or physically admixed with compositions prepared according to this invention.

The crystalline aluminosilicate prepared according to this invention may be incorporated as a pure material in a catalyst or adsorbent, or may be admixed with or incorporated within various binders or matrix materials depending upon the intended process use. The crystalline aluminosilicate can be combined with active or inactive materials, synthetic or naturally-occurring zeolites, as well as inorganic or organic materials which would be useful for binding the aluminosilicate. Well-known materials include silica, silica-alumina, alumina, alumina sols, hydrated aluminas, clays such as bentonite or kaolin, or other binders well known in the art. Typically, the aluminosilicate is incorporated within a matrix material by blending with a sol or gel of the matrix material and gelling the resulting mixture. Also, solid particles of the aluminosilicate and matrix material can be physically admixed. Typically, such aluminosilicate compositions can be pelletized or extruded into useful shapes. The crystalline aluminosilicate content can vary anywhere from a few up to 100 wt.% of the total composition. Typical catalytic compositions contain about 1 wt.% to about 100 wt.% crystalline aluminosilicate material and preferably contain about 2 wt.% to about 80 wt.% of such material.

Catalytic compositions comprising the crystalline aluminosilicate material of this invention and a suitable matrix material can be formed by adding a finely-divided crystalline aluminosilicate and a catalytically active metal compound to an aqueous sol or gel of the matrix material. The resulting mixture is thoroughly blended and gelled, typically, by adding a material such as ammonium hydroxide. The resulting gel can be dried and calcined to form a composition in which the crystalline aluminosilicate and catalytically active metal compound are distributed throughout the matrix material.

The crystalline aluminosilicates prepared according to this invention are useful as catalysts for various hydrocarbon conversion processes and are suitable for chemical adsorption. Some of the hydrocarbon conversion processes for which the aluminosilicates appear to have useful catalytic properties are fluidized catalytic cracking; hydrocracking; isomerization of normal paraffins and napthenes; reforming of naphthas and gasoline-boiling-range feedstocks; isomerization of alkylaromatics, such as xylenes; disproportionation of aromatics, such as toluene, to form mixtures of other more valuable products including benzene, xylene, and other higher methyl substituted benzenes; hydrotreating; alkylation, including (a) alkylation of benzene with ethylene, ethanol or other ethyl carbocation precursor to yield ethylbenzene, (b) alkylation of benzene or toluene with methanol or other methanol or carbocation precursor to yield xylenes, especially p-xylene, or pseudocumene, (c) alkylation of benzene with propylene and (d) alkylation of $C_3$ to $C_5$ paraffins with $C_5$ to $C_3$ olefins; hydrodealkylation; hydrodesulfurization; and hydrodenitrogenation. They are particularly suitable for the isomerization of alkylaromatics, such as xylenes, and for the conversion of ethylbenzene. Such aluminosilicates, in certain ion-exchanged forms, can be used to convert alcohols, such as methanol, to hydrocarbon products, such as aromatics or olefins.

The compositions prepared by this invention are especially suitable for hydrocarbon isomerization and disproportionation. It is especially useful for liquid or vapor phase isomerization of xylenes and particularly the isomerization of mixed xylenes to paraxylene products. Operating conditions for the isomerization of a xylene feed broadly comprise a temperature of about 95° C. to about 540° C., a hydrogen-to-hydrocarbon mole ratio of about 0 to about 20, a weight hourly space velocity (WHSV) of about 0.01 weight unit of feed per hour per weight unit of catalyst ($hr.^{-1}$) to about 90 $hr.^{-1}$, and a pressure of about 0 psig to about 1000 psig. Advantageously, the conditions comprise a temperature of about 250° C. to about 480° C., a hydrogen-to-hydrocarbon mole ratio of about 1 to about 12, and a WHSV of about 1 $hr.^{-1}$ to about 20 $hr.^{-1}$, and a pressure of about 0 psig to about 500 psig. The preferred conditions for the isomerization of xylenes comprise a temperature of about 315° C. to about 455° C., a hydrogen-to-hydrocarbon mole ratio of about 2 to about 8, a WHSV of about 1 $hr.^{-1}$ to about 10 $hr.^{-1}$, and a pressure of about 0 psig to about 300 psig. The choice of catalytically active metals to be placed on the crystalline aluminosilicate can be selected from any of those well known in the art. Nickel and molybdenum seem to be especially appropriate for isomerization of aromatics. When used as a catalyst in isomerization processes with suitable catalytically-active materials placed on the crystalline aluminosilicate, good selectivities for production of desired isomers are obtained.

When the crystalline aluminosilicate is used as a hydrocracking catalyst, hydrocracking charge stocks can pass over the catalyst at temperatures anywhere from about 260° C. to about 455° C. or higher using known molar ratios of hydrocarbon to hydrogen and varying pressures anywhere from a few up to many thousands of pounds per square inch or higher. The weight hourly space velocity and other process parameters can be varied consistent with the well-known teachings of the art.

The crystalline aluminosilicate also is suitable as a reforming catalyst to be used with the appropriate hydrogenation components as well-known reforming conditions including temperatures ranging from about 260° C. to 565° C. or more, pressures anywhere from a few up to 300 psig to 1000 psig, and weight hourly space velocities and hydrogen-to-hydrocarbon mole ratios consistent with those well known in the art.

The crystalline aluminosilicates also can be used as adsorbents to adsorb selectively specific isomers or hydrocarbons in general from a liquid or vapor stream.

The following Examples demonstrate but do not limit the present invention.

EXAMPLES I—XVI

Samples of crystalline aluminosilicate were prepared by dissolving measured quantities of sodium aluminate and sodium hydroxide in distilled water followed by a quantity of organic template. To this solution, 240 grams of Ludox HS-40 were added with vigorous stirring continuing for about 15 minutes after addition. The resulting curdy, gelatinous mixture was placed in a stirred, sealed crystallization vessel to crystalline for seven days. The resulting crystalline material was recovered by filtration, washed thoroughly with distilled water, and dried in a forced draft oven at 165° C. for 16 hours. The dried material was program calcined consisting of four hours from 200° F. (93° C.) to 1,000° F. (538° C.), four hours at 1,000° F. (538° C.), and at least four hours from 1,000° F. (538° C.) to 200° F. (93° C.). An X-ray diffraction spectrum of each preparation was taken to determine the crystalline form of each sieve. Details of the preparation of Examples I-XVI are shown in Table V.

Portions of sieve prepared in Examples I and VII were each exchanged with two times their weight of ammonium acetate in one liter of distilled water at 95° C. for 1.5 hours. The sieve then was filtered, washed with approximately 200 milliliters of distilled water, and filter dried. This procedure was repeated to obtain a total of five ammonium acetate exchanges with the last exchange receiving a wash of about 500 milliliters of water. The washed sieve was dried at 165° C. for approximately 16 hours (overnight). The dried sieve was program calcined with a program consisting of (a) a linear temperature rise of less than of equal to 200° F. per hour from 200° F. to 900° F., (b) holding at 900° F. for 4 hours, and (c) decreasing the temperature at a maximum of 200° F. per hour from 900° F. to 200° F. per hour. Ten grams of calcined sieve then were exchanged with $Ni(NH_3)_6^{++}$ with a solution containing 150 milliliters of 5% $Ni(NO_3)_2.6H_2O$ in distilled water to which was added approximately 20 milliliters of concentrated ammonium hydroxide. The pH of the exchange solution was 11.6. After exchanging for 2 hours at 90° C., the sieve was filtered from the exchange solution, washed with approximately 300 milliliters of distilled water and dried overnight in the forced draft oven at 165° C. The dried and exchanged sieve was program calcined at 900° F. with the program calcination procedure described above. The catalyst was prepared by dispersing the above calcined and exchanged sieve in PHF-alumina which is initially an acetic acid stabilized alumina hydrosol containing about 8.7% $Al_2O_3$. To 11.1 grams of calcined and exchanged sieve was added 12.8 grams of distilled water to fill the sieve pores with water. The wet sieve was then added and thoroughly mixed with 68.7 grams of alumina hydrosol. The mixture was gelled (solidified) with the addition of a solution containing 3.5 milliliters of distilled water and 3.5 milliliters of concentrated ammonium hydroxide. The resulting solid was then dried overnight in a forced air oven at 165° C. The dried solid was program calcined at 900° F. with the program as described above. The calcined solid was crushed and sized to 30 to 50 mesh (U.S. Sieve Series) and recalcined with the above 900° F. program calcination.

One gram of 30–50 mesh aluminosilicate material was placed in a small screening reactor and sulfided by contacting it with $H_2S$ gas at room temperature. The sulfided catalyst was heat treated at 314° C. for one hour in hydrogen at 150 psig. A hydrocarbon feed was passed on a once-through operation over the catalyst at 150 psi, 427° C., a molar ratio of hydrogen to hydrocarbon of 6.5 and a space velocity (WHSV) of 5.9. After about 138 hours on stream, feed and liquid effluents were analyzed and results were calculated. Results from the catalyst prepared using the sieve of Example I are shown in Table VI while results from the catalyst prepared using the sieve of Example VII are shown in Table VII. Because of equipment limitations on the screening unit, only the liquid analysis is shown. The catalyst was effective in producing paraxylene from other aromatics in the feed stream.

TABLE V

| Example | I | II | III | IV | V | VI | VII | VIII |
|---|---|---|---|---|---|---|---|---|
| Water (grams) | 1,200 | 600 | 1,250 | 1,000 | 1,200 | 1,200 | 300 | 1200 |
| Sodium Hydroxide (grams) | 10.0 | 6.0 | 10.0 | 10.0 | 10.0 | 12.0 | 2.5 | 12 |
| Sodium aluminate (grams) | 20.0 | 10.0 | 40.0 | 10.0 | 20.0 | 20.0 | 2.4 | 40 |
| Template | Triethanolamine (240 grams) | Morpholine (180 grams) | 2-amino-2-ethyl-1,3-propanediol (240 grams) | Dioxane (400 grams) | Morpholine (240 grams) | Morpholine (240 grams) | Morpholine (57.0 grams) | Morpholine (240 grams) |
| Ludox HS-40 (grams) | 240 | 120 | 242 | 250 | 240 | 240 | 57.5 | 240 |
| Initial pH | 12.7 | 13.7 | — | 13.5 | 12.8 | 13.2 | — | 13.3 |
| Crystalline Form | Mordenite | Mordenite 60% Ferrierite 40% | Mordenite[1] | Mordenite[2] | Mordenite | Mordenite | Ferrierite | Table III |

| Example | IX | X | XI | XII | XIII | XIV | XV | XVI |
|---|---|---|---|---|---|---|---|---|
| Water (grams) | 210 | 500 | 600 | 1200 | 1200 | 1200 | 500 | 1200 |
| Sodium Hydroxide (grams) | 1.7 | 4.0 | 4.8 | 6.0 | 12.0 | 10.0 | 10.0 | 12.0 |
| Sodium aluminate (grams) | 1.8 | 16.0 | 19.2 | 10.0 | 9.6 | 5.0 | 5.0 | 10.0 |
| Template | Dioxane (40 grams) | Morpholine (95.7 grams) | Morpholine (115.0 grams) | Morpholine (240 grams) | Morpholine (191 grams) | Triethanolamine (240 grams) | Dioxane (200 grams) | Morpholine (240 grams) |
| Ludox HS-40 (grams) | 41.4 | 95.5 | 114.0 | 240 | 191 | 240 | 250 | 240 |
| Initial pH | 10.3 | 12.7 | 12.8 | 12.6 | — | 12.7 | 13.0 | 13.3 |
| Crystalline | Ferrierite[2] | Ferrierite | Ferrierite[3] | Ferrierite | Table IV | Table IV | Ferrierite[2] | Ferrierite |

TABLE V-continued

Form (1) contained minor amount of analcime
(2) contained minor amount of alpha-quartz
(3) Contained about 30% other crystalline material.

TABLE VI

| Components (wt. %) | Feed | After Reaction |
|---|---|---|
| Paraffins and Napthenes | 0.20 | 0.24 |
| Benzene | 0.003 | 4.45 |
| Toluene | 0.06 | 10.85 |
| Ethylbenzene | 19.33 | 9.74 |
| p-Xylene | 9.61 | 14.59 |
| m-Xylene | 47.47 | 31.34 |
| o-Xylene | 23.37 | 13.72 |
| Percent Approach to Theoretical Equilibrium (%) | | |
| p-Xylene | | 108.9 |
| m-Xylene | | 94.0 |
| o-xylene | | 130.9 |
| Ethylbenzene Conversion (%) | | 49.6 |

TABLE VII

| | | Test Runs | | |
|---|---|---|---|---|
| | | 1 | 2 | 3 |
| Conditions | | | | |
| Reactor Temp. (°F.) | | 740 | 760 | 780 |
| Reactor Pressure (psig) | | 150 | 150 | 150 |
| Space Velocity (WHSV, hr$^{-1}$) | | 5.59 | 5.94 | 5.32 |
| Hydrogen/hydrocarbon (molar ratio) | | 6.8 | 6.4 | 7.2 |
| Components (wt %) | Feed | | | |
| Paraffins and Naphthenes | — | 0.11 | 0.07 | 0.09 |
| Benzene | — | 5.80 | 6.45 | 8.14 |
| Toluene | 0.07 | 1.70 | 1.71 | 2.03 |
| Ethylbenzene | 18.40 | 9.68 | 9.50 | 6.66 |
| p-Xylene 10.10 | | | | |
| m-Xylene 46.44 | 81.00 | 80.46 | 80.86 | 81.49 |
| o-Xylene 24.06 | | | | |
| C$_9^+$ | 0.53 | 2.25 | 1.91 | 1.59 |
| Results(1) | | | | |
| PATE - | | | | |
| p-Xylene | | 76.1 | 76.9 | 83.3 |
| m-Xylene | | 89.0 | 87.8 | 93.8 |
| o-Xylene | | 60.0 | 62.7 | 69.1 |
| Ethylbenzene conversion (%) | | 47.4 | 51.1 | 63.8 |
| Xylene Loss (%) | | 0.667 | 0.173 | −0.605 |

(1)PATE = Percent Approach to Theoretical Equilibrium

I claim:

1. A method to prepare a mordenite, ferrierite, ZSM-4 or ZSM-5 crystalline aluminosilicate molecular sieve comprising (1) forming an aqueous mixture of sources for an oxide of aluminum and an oxide of silicon, a cation and an alkali metal cation-complexed ether wherein the composition of the mixture of initial reactants in terms of mole ratios of oxides is:

| SiO$_2$/Al$_2$O$_3$ | 8–80 |
|---|---|
| R$_2$O$^+$(R$_2$O$^+$ + M$_{2/n}$O) | 0.2–0.95 |
| OH$^-$/SiO$_2$ | 0.01–3 |
| H$_2$O/OH$^-$ | 10–500 | where R is an alkali metal cation-complexed ether and M is at least one cation having a valence n, (2) maintaining the pH of such mixture between about 9 and about 14 and (3) crystallizing such mixture at a pressure at least the vapor pressure of water for about 0.25 to about 20 days at about 125° to about 200° C.

2. The method of claim 1 wherein source for the oxide of aluminum is sodium aluminate.

3. The method of claim 1 wherein the composition of the mixture of initial reactants in terms of mole ratios of oxides is:

| SiO$_2$/Al$_2$O$_3$ | 15–80 |
|---|---|
| R$_2$O+/[R$_2$O+ + M$_{2/n}$O] | 0.2–0.95 |
| OH$^-$/SiO$_2$ | 0.01–3 |
| H$_2$O/OH$^-$ | 10–500 | where R is an alkali metal cation-complexed ether and M is at least one cation of valence n.

4. The method of claim 1 wherein the crystalline aluminosilicate is mordenite-like.

5. The method of claim 1 wherein the crystalline aluminosilicate is ferrierite-like.

6. The method of claim 1 wherein the crystalline aluminosilicate is mordenite-like.

7. The method of claim 3 wherein the crystalline aluminosilicate is ferrierite-like.

8. The method of claim 1 wherein the silica/alumina ratio of initial reactants is about 16.

9. The method of claim 3 wherein the silica/alumina ratio of initial reactants is about 32.

10. The method of claim 1 wherein the cation-complexed ether is dioxane complexed sodium ion.

11. The method of claim 1 wherein the pH of the mixture is maintained between about 10.5 and about 13.

12. The method of claim 1 wherein the crystallizing mixture is maintained at about 125° C. to about 200° C. for about one to about seven days.

13. The method of claim 1 wherein M is an alkali metal or alkaline earth metal cation.

14. The method of claim 1 wherein source for the oxide of silicon is a silicic acid polymer.

15. The method of claim 1 wherein a catalytically active material is placed onto the crystalline aluminosilicate.

16. The method of claim 15 wherein the catalytically active material is ion exchanged onto the crystalline aluminosilicate.

17. The method of claim 16 wherein the catalytically active material is hydrogen, metal ions of Groups IB, IIB, IIIA or VIII or of manganese, vanadium, chromium, uranium or rare earth elements.

18. The method of claim 25 wherein the ion is nickel ion.

19. The method of claim 17 wherein a catalytically active compound is impregnated onto the mordenite crystalline aluminosilicate.

20. The method of claim 19 wherein the catalytically active compound is a water soluble salt of metals of Groups IB, IIB, IIIA, IVB, VB, VIB, VIIB, or VIII, or rare earth elements.

21. The method of claim 20 wherein the catalytically active compound is a salt of molybdenum.

22. The method of claim 1 wherein the prepared molecular sieve is incorporated within a suitable matrix material.

23. The method of claim 22 wherein the matrix material is silica, silica-alumina or alumina.

24. The method of claim 1 wherein the prepared crystalline aluminosilicate shows the X-ray diffraction lines contained in Table IV of the specification.

25. The method of claim 1 wherein the prepared crystalline aluminosilicate shows the X-ray diffraction lines contained in Table V of the specification.

26. The method of claim 1 wherein the alkali metal cation-complexed ether is an ether containing up to about twelve carbon atoms complexed with a Group IA metal cation.

27. The method of claim 26 wherein the ether is a cyclic ether.

28. The method of claim 26 wherein the ether is tetrahydroxyfuran, dioxane, dioxolane or a crown ether.

* * * * *